United States Patent
Segel et al.

(10) Patent No.: US 7,571,005 B1
(45) Date of Patent: Aug. 4, 2009

(54) ADAPTIVE PLACE-PITCH RANKING PROCEDURE FOR OPTIMIZING PERFORMANCE OF A MULTI-CHANNEL NEURAL STIMULATOR

(75) Inventors: Philip A Segel, Englewood, CO (US); Tracey L. Kruger, Chatsworth, CA (US); Leonid M Litvak, Los Angeles, CA (US)

(73) Assignee: Advanced Bionics, LLC, Valencia, CA (US)

( * ) Notice: Subject to any disclaimer, the term of this patent is extended or adjusted under 35 U.S.C. 154(b) by 319 days.

(21) Appl. No.: 11/469,820

(22) Filed: Sep. 1, 2006

Related U.S. Application Data

(63) Continuation-in-part of application No. 10/819,611, filed on Apr. 7, 2004, now Pat. No. 7,103,417.

(60) Provisional application No. 60/464,222, filed on Apr. 18, 2003.

(51) Int. Cl.
  *A61N 1/36* (2006.01)
  *A61F 11/04* (2006.01)
  *A61F 11/00* (2006.01)

(52) U.S. Cl. ............ 607/57; 607/55; 607/56; 607/137; 600/559

(58) Field of Classification Search ............ 607/55–57; 600/559; 381/320; 73/585
See application file for complete search history.

(56) References Cited

U.S. PATENT DOCUMENTS

| | | | |
|---|---|---|---|
| 5,626,629 A | * | 5/1997 | Faltys et al. .................. 607/57 |
| 5,649,970 A | * | 7/1997 | Loeb et al. .................... 607/57 |
| 6,157,861 A | * | 12/2000 | Faltys et al. .................. 607/57 |
| 6,308,102 B1 | * | 10/2001 | Sieracki et al. ............... 607/59 |
| 7,006,646 B1 | * | 2/2006 | Baechler .................... 381/314 |

* cited by examiner

*Primary Examiner*—Carl H. Layno
*Assistant Examiner*—Tammie K. Heller
(74) *Attorney, Agent, or Firm*—Bryant R. Gold

(57) ABSTRACT

An adaptive place-pitch ranking procedure for use with a cochlear implant or other neural stimulation system provides a systematic method for quantifying the magnitude and direction of errors along the place-pitch continuum. The method may be conducted and completed in a relatively short period of time. In use, the implant user or listener is asked to rank the percepts obtained after a sequential presentation of monopolar stimulation pulses are applied to a selected spatially-defined electrode pair. The spatially-defined electrode pair may be a physical electrode pair or a virtual electrode pair. A virtual electrode pair includes at least one virtual electrode contact. Should the patient's judgment of pitch order be correct for all applied interrogations, then no further testing involving the tested electrode pair (two electrode contacts) is undertaken. However, should there be errors in the place-pitch ranking, which errors evidence perceptual place-confusions, then a search is undertaken for the spread of the perceptual confusion. This search for the spread of confusion continues until no errors are made in all directions. Identified channels wherein pitch confusion exists may be de-selected (not used) during normal operation of the cochlear implant or other neural stimulation system.

6 Claims, 7 Drawing Sheets

FIG. 4B

| | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| 1 | ░ | LH | S | S | LH | | | | | | | | | | | |
| 2 | S | ░ | S | L | L | | | | | | | | | | | | 
| 3 | HL | LH | ░ | LH | LH | | | | | | | | | | | |
| 4 | S | L | S | ░ | LH | | | | | | | | | | | |
| 5 | LH | LH | LH | LH | ░ | LH | | | | | | | | | | |
| 6 | | | | | LH | ░ | LH | | | | | | | | | |
| 7 | | | | | | LH | ░ | LH | | | | | | | | |
| 8 | | | | | | | LH | ░ | LH | | | | | | | |
| 9 | | | | | | | | LH | ░ | LH | | | | | | |
| 10 | | | | | | | | | LH | ░ | LH | | | | | |
| 11 | | | | | | | | | | LH | ░ | LH | | | | |
| 12 | | | | | | | | | | | LH | ░ | LH | | | |
| 13 | | | | | | | | | | | | LH | ░ | LH | | |
| 14 | | | | | | | | | | | | | LH | ░ | LH | |
| 15 | | | | | | | | | | | | | | LH | ░ | LH |
| 16 | | | | | | | | | | | | | | | LH | ░ |

ADAPTIVE PLACE-PITCH RANKING PROCEDURE FOR OPTIMIZING PERFORMANCE OF A MULTI-CHANNEL NEURAL STIMULATOR

The present application is a Continuation-in-Part of U.S. patent application Ser. No. 10/819,611, filed Apr. 7, 2004, to be issued as U.S. Pat. No. 7,103,417 on Sep. 5, 2006; which application claims the benefit of U.S. Provisional Patent Application Ser. No. 60/464,222, filed Apr. 18, 2003, which applications and patent are incorporated herein by reference.

BACKGROUND OF THE INVENTION

The present disclosure relates to neural stimulators, e.g., cochlear implants, and more particularly to a technique for optimizing the number of channels a cochlear or other neural implant system should employ in order to enhance the performance of the implant system. In the case of a cochlear implant system, the present disclosure optimizes the number of channels the cochlear implant should use in order to enhance a user's ability to perceive and understand sound.

Electrical stimulation of predetermined locations within the cochlea of the human ear through an intra-cochlear electrode array is described, e.g., in U.S. Pat. No. 4,400,590. The electrode array shown in the '590 patent comprises a plurality of exposed electrode pairs spaced along and imbedded in a resilient curved base for implantation in accordance with a method of surgical implantation, e.g., as described in U.S. Pat. No. 3,751,615. The system described in the '590 patent receives audio signals, i.e., sound waves, at a signal processor (or speech processor) located outside the body of a hearing impaired patient. The speech processor converts the received audio signals into modulated RF data signals that are transmitted by a cable connection through the patient's skin to an implanted multi-channel intracochlear electrode array. The modulated RF signals are demodulated into analog signals and are applied to selected ones of the plurality of exposed electrode pairs in the intra-cochlear electrode so as to electrically stimulate predetermined locations of the auditory nerve within the cochlea.

U.S. Pat. No. 5,938,691, incorporated herein by reference, shows an improved multi-channel cochlear stimulation system employing an implanted cochlear stimulator (ICS) and an externally wearable speech processor (SP). The speech processor employs a headpiece that is placed adjacent to the ear of the patient, which receives audio signals and transmits the audio signals back to the speech processor. The speech processor receives and processes the audio signals and generates data indicative of the audio signals for transcutaneous transmission to the implantable cochlear stimulator. The implantable cochlear stimulator receives the transmission from the speech processor and applies stimulation signals to a plurality of cochlea stimulating channels, each having a pair of electrodes in an electrode array associated therewith. Each of the cochlea stimulating channels uses a capacitor to couple the electrodes of the electrode array.

Other improved features of a cochlear implant system are taught, e.g., in U.S. Pat. Nos. 5,626,629; 6,067,474; 6,157,861; 6,219,580; 6,249,704; and 6,289,247, each of which patents is incorporated herein by reference. Further enhancements are disclosed, e.g., in pending and co-owned U.S. patent application Ser. No. 10/218,645, filed Aug. 13, 2002, and U.S. patent application Ser. No. 10/218,616, filed Aug. 13, 2002, each of which patent applications is also incorporated herein by reference.

The implantable cochlear stimulators described in the '629, '474, '861 and '580 patents are also able to selectively control the pulse width of stimulating pulses that are applied through the electrode array to the cochlea, as well as the frequency at which the stimulating pulses are applied.

New generation cochlear implants have enhanced processing power, and can provide multiple platforms for delivering electrical stimuli to the auditory nerve. This includes the ability to deliver high frequency pulsitile stimulation made up of current pulses of controlled amplitude, width and frequency. Such new generation cochlear implants are frequently referred to as a "bionic ear" implant.

As the art of cochlear stimulation has advanced to produce bionic ear implants, the implanted portion of the cochlear stimulation system, and the externally wearable processor (or speech processor) have become increasingly complicated and sophisticated. Much of the circuitry previously employed in the externally wearable processor has been moved to the implanted portion, thereby reducing the amount of information that should be transmitted from the external wearable processor to the implanted portion.

As the complexity of the bionic ear implants has increased, the amount of control and discretion exercisable by an audiologist in selecting the modes and methods of operation of the cochlear stimulation system has also increased dramatically. For example, it is no longer possible to fully control and customize the operation of the cochlear stimulation system through the use of, for example, switches located on the speech processor. As a result, it has become optional to utilize an implantable cochlear stimulator fitting system to establish the operating modes and methods of the cochlear stimulation system and then to download such programming into the speech processor. One such fitting system is described in the '629 patent. An improved fitting system is described in the '247 patent.

The '247 patent, in addition to showing an improved fitting system, also highlights representative stimulation strategies that may be employed by a multichannel stimulation system. Such strategies represent the manner or technique in which the stimulation current is applied to the electrodes of an electrode array used with the stimulation system. Such stimulation strategies, all of which apply current pulses to selected electrodes, may be broadly classified as: (1) sequential or non-simultaneous (where only one electrode pair receives a current pulse at the same time); (2) simultaneous (where the electrodes associated with more than one channel receive current stimuli at the same time); or (3) partially simultaneous pulsitile stimulation (where only a select grouping of the electrodes receive stimuli at the same time in accordance with a predefined pattern).

Recognition of speech sounds by cochlear implant recipients is based upon the ability of the sound processor to represent the time-varying acoustic patterns such that the listener can resolve the critical temporal and spectral characteristics of those acoustic patterns. Differences in how speech sounds are made are reflected in the acoustic spectrum. These acoustic cues contain the manner in which a sound is made in the vocal tract, the place at which the vocal tract constricts the airstream in the oral cavity and whether or not the sound's production involves vocal fold vibration.

In cochlear implant processors, the above-described spectral cues are distributed across some number of channels. In modern cochlear processors the number of channels selected for a stimulation sequence can exceed 12-15, with various degrees of simultaneity in terms of data presentation. While this may allow for the allocation of spectral details to be transmitted to the auditory nerve along a large number of physical channels, problems such as spatial channel interaction and the inability to resolve place of stimulation among adjacent channels may actually lead to poorer discrimination. That is, systematic assessment of phoneme recognition by cochlear implant users has shown that while the features of manner of articulation and voicing are well transmitted, place cues are less well resolved. As a result, it has been determined that having a greater number of stimulation channels by itself is not always sufficient to provide improved understanding. To the contrary, in some instances, increasing the number of channels has actually caused a decrease in the user's understanding. Hence, it is seen that what is needed is a clinically relevant way of optimizing the number of channels that are used by the cochlear implant system so that the user's ability to improve understanding is maximized.

While assessing spatial (as well as temporal) channel interaction could be helpful in optimizing channels to be used in a stimulation sequence, the procedures to carry out such assessment are far too cumbersome to be used clinically. An easier way to look at the issue of spectral confusion among adjacent stimulation channels is to determine the implant user's ability to differentiate channels based upon the perceived pitch derived from the place of stimulation. While clinical procedures do exist for "rating" (same/different task), "ranking" (high/low) or "scaling" (numerical estimation) the pitch perceived by stimulating channels along an electrode array, such procedures do not provide a systematic method for quantifying the magnitude and direction of errors along the place-pitch continuum. Without such a method or technique, the reduction or re-ordering of stimulation channels may only be accomplished in a haphazard way, thereby penalizing patient performance. What is needed, therefore, is a method or technique for systematically identifying an optimum number and/or an optimum ordering of stimulation channels along the place-pitch continuum so that the patient's performance may be enhanced.

SUMMARY OF THE INVENTION

The present disclosure addresses the above and other needs by providing an adaptive place-pitch ranking procedure for use within a cochlear implant system. Such adaptive place-pitch ranking procedure provides a systematic method for quantifying the magnitude and direction of errors along the place-pitch continuum. Moreover, the procedure is clinically feasible, i.e., the procedure may be conducted and completed in a relatively short period of time.

The adaptive place-pitch ranking procedure may be summarized as set forth in the following paragraphs:

The implant listener is asked to rank the percepts obtained after a sequential presentation of pulse trains, pulse bursts or noise stimuli are applied to his or her auditory nerve through his or her bionic ear (or equivalent) cochlear implant system. All of the stimuli and recording media that are applied to the implant listener's auditory nerve may be generated through a software module installed within the cochlear implant processor fitting system.

As the stimuli are applied, adjacent channels are stimulated alternately. The choice of electrode contacts through which the stimuli are applied is randomly ordered via a computer-generated sequence. Each electrode pair is interrogated at least 4 times, e.g., two ordinal positions for each of two presentation orders.

Should the patient's judgment of pitch order be correct for all applied interrogations, e.g., for all four combinations, then no further testing involving the tested electrode pair (two electrode contacts) is undertaken. However, should there be errors in the place-pitch ranking, which errors evidence perceptual place-confusions, then a search is undertaken for the spread of the perceptual confusion by separating the target channel and competing channel by one electrode contact at a time. This search for the spread of confusion continues until no errors are made in all directions.

Pre-training trials employing channels separated by a large spatial distance (e.g., up to 14 mm) may be employed as needed. During such pre-training trials, a number of "foils" may be introduced during the stimulation procedure wherein the same contact is stimulated twice. This is done in order to separate true perceptual errors from errors in performing the task.

Responses obtained during the stimulation procedure are recorded on a grid after each stimulus pair has been presented. Responses are made based on the listener's perception of which stimulus or stimulus sequence elicits the "highest" pitch. Acceptable responses from the listener, for example, may be "first", "second", or "same". The listener may ask for repetition of the stimulus sequence, if necessary.

The adaptive place-pitch ranking procedure described herein may be used in, or applied to, a wide variety of clinical use cases, including (but not limited to) the following clinical use cases:

1. Place-pitch ranking conducted in one ear using a unilateral cochlear implant;
2. Place-pitch ranking conducted in one ear using a combined acoustic and electric processor;
3. Place-pitch ranking conducted across ears, i.e., using bilateral cochlear implants where the target and competing channels are in different ears;
4. Place-pitch ranking conducted across ears, i.e., using bilateral hearing prosthetics where one ear has a cochlear prosthetic and the other ear is fitted with a different sensory aid, such as a conventional hearing aid or equivalent instrument.

Further, the adaptive place-pitch ranking procedure described herein is not limited in its resolution to the physical separation distances between the physical electrodes used on the electrode array. Rather, "virtual" electrodes may be employed which provide a much finer resolution for ascertaining the spread of perceptual confusion, when such finer resolution is needed.

BRIEF DESCRIPTION OF THE DRAWINGS

The above and other aspects, features and advantages of the procedure described herein will be more apparent from the following more particular description thereof, presented in conjunction with the following drawings and Appendix wherein:

FIG. 4B shows exemplary data of the type that may be collected in the matrix or grid table of FIG. 4A as the adaptive place-pitch ranking procedure is carried out;

Figure 1:
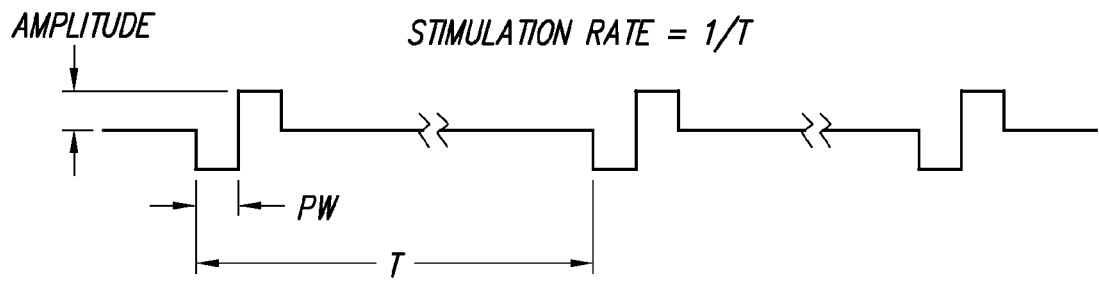
FIG. 1 is a current stimulation waveform that defines the stimulation rate (1/T) and biphasic pulse width (PW) associated with electrical stimuli, as those terms are used in the present application.

Appendix A provides an overview of one embodiment of a Fitting System that may be used with the present procedure described herein.

Corresponding reference characters indicate corresponding components throughout the several views of the drawings.

DETAILED DESCRIPTION OF THE INVENTION

The following description is of the best mode presently contemplated for carrying out the place-pitch ranking procedure described herein. This description is not to be taken in a limiting sense, but is made merely for the purpose of describing the general principles of the procedure. The scope of Applicants' invention should be determined with reference to the claims.

Figure 2A:
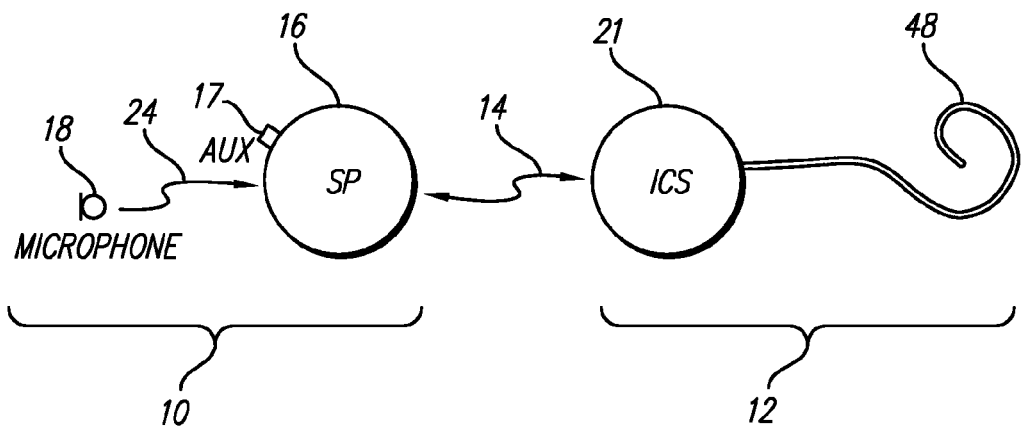
FIGS. 2A and 2B respectively show a cochlear implant system and a partial functional block diagram of the cochlear stimulation system, which system is capable of providing high rate pulsitile electrical stimuli.
Figure 2B:
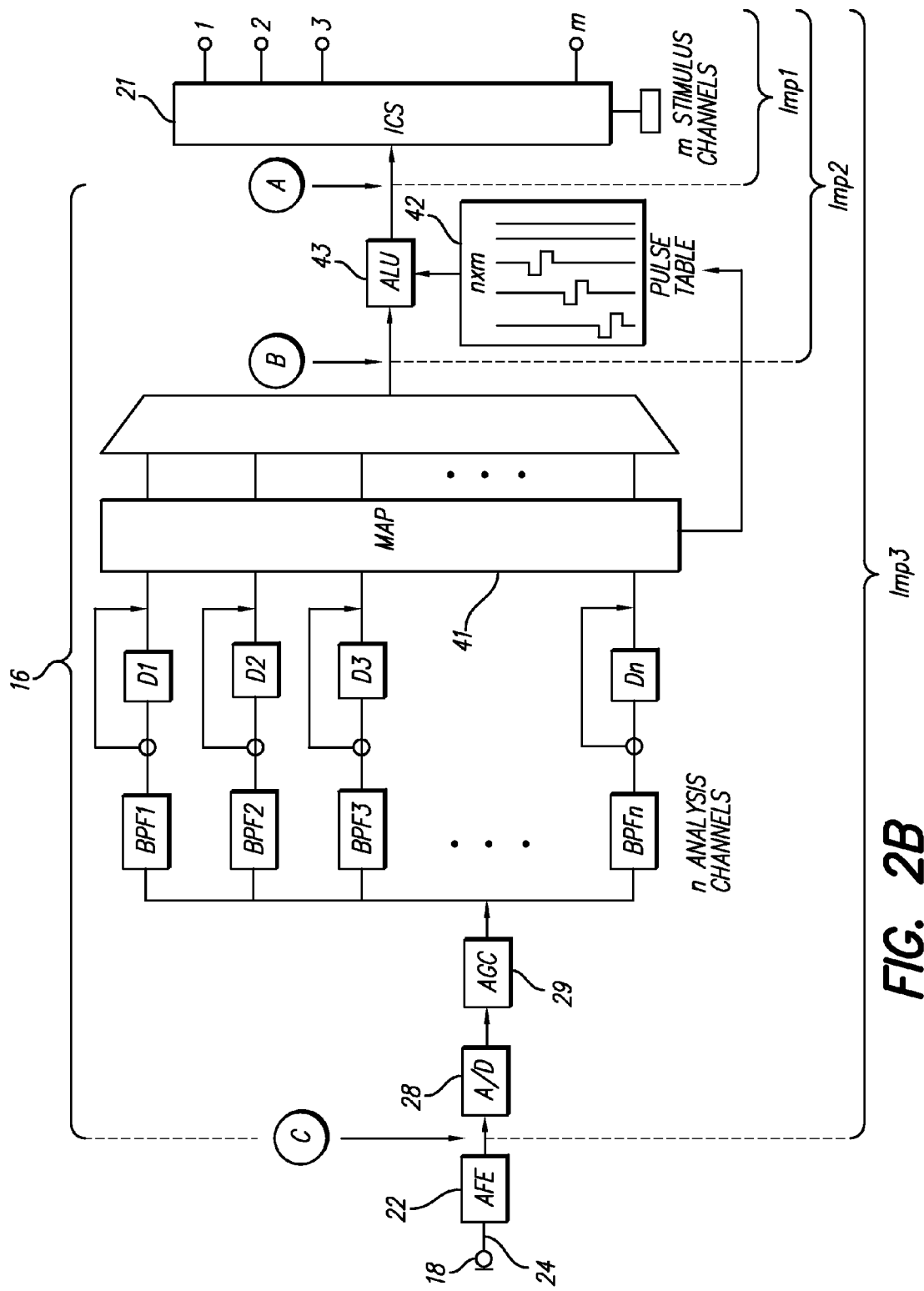

The present disclosure—a place-pitch ranking procedure that identifies when pitch confusion exists between neighboring channels of a multi-channel implant system so that use of such channels can be avoided or minimized—is described primarily in connection with FIGS. 3-6. The description of FIGS. 1, 2A and 2B, presented first, provides an overview of a representative cochlear implant system that may be used to practice the place-pitch ranking procedure described in connection with FIGS. 3-6. As such, it is to be emphasized that FIGS. 1, 2A and 2B do not describe the procedure, per se, but rather describe a hardware/software platform on which the procedure may be practiced. It should also be emphasized that use of the present procedure is not limited to a cochlear implant system—a bionic ear implant system—of the type described in FIGS. 1, 2A and 2B. Rather, the procedure may be practiced with any cochlear implant system, or neural stimulation system, where pitch confusion in adjacent channels, or stimulus-frequency channel cross-over, is or may be a problem.

FIG. 1 shows a waveform diagram of a biphasic pulse train, and defines stimulation rate, pulse width and pulse amplitude as those terms are commonly used in connection with a cochlear implant or other neural stimulation system.

FIG. 2A shows a bionic ear cochlear stimulation system that includes a sound processor portion 10 (which may also be referred to as a "speech processor", but a "sound processor" is more descriptive of the function performed because it is more than just "speech" that is processed) and a cochlear stimulation portion 12. The sound processor portion 10 includes a sound processor (SP) 16 and a microphone 18. The microphone 18 may be connected directly to the SP 16, or may be coupled to the SP 16 through an appropriate communication link 24. The cochlear stimulation portion 12 includes an implantable cochlear stimulator (ICS) 21, and an electrode array 48. The electrode array 48 is adapted to be inserted within the cochlea of a patient. The array 48 includes a multiplicity of electrodes, e.g., sixteen electrodes, spaced along its length that are selectively connected to the ICS 21. The electrode array 48 may be substantially as shown and described in U.S. Pat. No. 4,819,647 or 6,129,753, incorporated herein by reference. Electronic circuitry within the ICS 21 allows a specified stimulation current to be applied to selected pairs or groups of the individual electrodes included within the electrode array 48 in accordance with a specified stimulation pattern, defined by the SP 16.

The ICS 21 and the SP 16 are shown in FIG. 2A as being linked together electronically through a suitable data or communications link 14. In some cochlear implant systems, the SP 16 and microphone 18 comprise the external portion of the cochlear implant system; and the ICS 21 and electrode array 48 comprise the implantable portion of the system. Thus, the data link 14 is a transcutaneous data link that allows power and control signals to be sent from the SP 16 to the ICS 21. In some embodiments, data and status signals may also be sent from the ICS 21 to the SP 16.

In a typical bionic ear or other cochlear implant system, as shown more particularly below in FIG. 2B, at least certain portions of the SP 16 are included within the implantable portion of the overall cochlear implant system, while other portions of the SP 16 remain in the external portion of the system. In general, at least the microphone 18 and associated analog front end (AFE) circuitry 22 will be part of the external portion of the system; and at least the ICS 21 and electrode array 48 are part of the implantable portion. As used herein, "external" means not implanted under the skin or residing within the inner ear. However, "external" may mean within the outer ear, including in the ear canal, and may also include within the middle ear.

Typically, where a transcutaneous data link is to be established between the external portion and implantable portions of the system, such link is realized by an internal antenna coil within the implantable portion, and an external antenna coil within the external portion. In use, the external antenna coil is positioned so as to be aligned over the location where the internal antenna coil is implanted, allowing such coils to be inductively coupled to each other, thereby allowing data (e.g., the magnitude and polarity of a sensed acoustic signals) and power to be transmitted from the external portion to the implantable portion. Note, in other embodiments, both the SP 16 and the ICS 21 may be implanted within the patient, either in the same housing or in separate housings. If in the same housing, the link 14 may be realized with a direct wire connection within such housing. If in separate housings, as taught, e.g., in U.S. Pat. No. 6,067,474, incorporated herein by reference, the link 14 may be an inductive link using a coil or a wire loop coupled to the respective parts.

The microphone 18 senses acoustic signals (sound) and converts such sensed signals to corresponding electrical signals, and may thus be considered as an acoustic transducer. The electrical signals are sent to the SP 16 over a suitable electrical or other link 24. The SP 16 processes these converted acoustic signals in accordance with a selected speech processing strategy in order to generate appropriate control signals for controlling the ICS 21. Such control signals specify or define the polarity, magnitude, location (which electrode pair receives the stimulation current), and timing (when the stimulation current is applied to the electrode pair) of the stimulation current that is generated by the ICS. Such control signals thus combine to produce a desired spatiotemporal pattern of electrical stimuli in accordance with the desired speech processing strategy.

The speech processing strategy is used, inter alia, to condition the magnitude and polarity of the stimulation current applied to the implanted electrodes of the electrode array 48. Such speech processing strategy involves defining a pattern of stimulation waveforms that are to be applied to the electrodes as controlled electrical currents. For example, an auto-conditioning with high resolution (ACHR) strategy may be used which stimulates the implanted electrodes with a high rate pulsitile pattern that is amplitude modulated by the sound information. If multiple electrode pairs exist, as is the case with a multichannel cochlear implant system, then the types of stimulation patterns applied to the multiple channels may be conveniently categorized as: (1) simultaneous stimulation patterns, or (2) non-simultaneous stimulation patterns. Simultaneous stimulation patterns may be "fully" simultaneous or partially simultaneous. A fully simultaneous stimulation pattern is one wherein stimulation currents, either analog or pulsitile, are applied to the electrodes of all of the available channels at the same time. A partially simultaneous stimulation pattern is one wherein stimulation currents, either analog or pulsitile, are applied to the electrodes of two or more channels, but not necessarily all of the channels, at the same time. Examples of each type are given in U.S. Pat. No. 6,289,247, previously incorporated herein by reference.

Analog waveforms used in analog stimulation patterns are typically reconstructed by the generation of continuous short monophasic pulses (samples). The sampling rate is selected to be fast enough to allow for proper reconstruction of the temporal details of the signal. An example of such a sampled analog stimulation pattern is a simultaneous analog sampler (SAS) strategy.

Current pulses applied in pulsitile stimulation patterns are generally biphasic pulses, as shown in FIG. 1, but may also be multiphasic pulses, applied to the electrodes of each channel. The biphasic/multiphasic pulse has a magnitude (e.g., amplitude and/or duration) that varies as a function of the sensed acoustic signal. (A "biphasic" pulse is generally considered as two pulses: a first pulse of one polarity having a specified magnitude, followed immediately, or after a very short delay, by a second pulse of the opposite polarity having the same total charge, which charge is the product of stimulus current times duration of each pulse or phase.) For multichannel cochlear stimulators, it is common to apply a high rate biphasic stimulation pulse train to each of the pairs of electrodes of selected channels in accordance with a selected strategy, and modulate the pulse amplitude of the pulse train as a function of information contained within the sensed acoustic signal.

Turning next to FIG. 2B, a partial block diagram of a representative bionic ear cochlear implant is shown. More particularly, FIG. 2B shows a partial functional block diagram of the SP 16 and the ICS 21 of an exemplary bionic ear cochlear implant system capable of providing a high rate pulsitile stimulation pattern. That which is shown in FIG. 2B depicts the functions that are carried out by the SP 16 and the ICS 21. The actual electronic circuitry used to carry out these functions is not critical to understanding and practicing the procedures described herein. It should also be pointed out that the particular functions shown in FIG. 2B are representative of just one type of signal processing strategy that may be employed (which divides the incoming signal into frequency bands, and independently processes each band). Other signal processing strategies could just as easily be used to process the incoming acoustical signal.

A complete description of the functional block diagram of the bionic ear implant shown in FIG. 2B is found in U.S. Pat. No. 6,219,580, previously incorporated herein by reference. It is to be emphasized that the bionic ear functionality shown in FIG. 2B is only representative of one type of exemplary bionic ear implant, and is not intended to be limiting. The details associated with a given bionic ear implant are not critical to understanding and practicing the procedures described herein.

In the manner described in the U.S. Pat. No. 6,219,580, the bionic ear implant functionally shown in FIG. 2B provides n analysis channels that may be mapped to one or more stimulus channels. That is, as seen in FIG. 2B, after the incoming sound signal is received through the microphone 18 and processed in the analog front end circuitry (AFE) 22, it is digitized in an analog to digital (A/D) converter 28, and then subjected to appropriate gain control (which may include compression) in an automatic gain control (AGC) unit 29. After appropriate gain control, the signal is divided into n analysis channels, each of which includes a bandpass filter, BPFn, centered at a selected frequency. The signal present in each analysis channel is processed as described more fully in the U.S. Pat. No. 6,219,580, and the signals from each analysis channel are then mapped, using mapping function 41, so that an appropriate stimulus current, of a desired amplitude and timing, may be applied through a selected stimulus channel to stimulate the auditory nerve.

Thus it is seen that the system of FIG. 2B provides a multiplicity of channels, n, wherein the incoming signal is analyzed. The information contained in these n "analysis channels" is then appropriately processed, compressed and mapped in order to control the actual stimulus patterns that are applied to the patient by the ICS 21 and its associated electrode array 48. The electrode array 48 includes a multiplicity of electrode contacts, connected through appropriate conductors, to respective current generators, or pulse generators, within the ICS. Through these multiplicity of electrode contacts, a multiplicity of stimulus channels, e.g., m stimulus channels, exist through which individual electrical stimuli may be applied at m different stimulation sites within the patient's cochlea. The present procedure focuses on a technique or method for clinically determining an optimum number m of stimulus channels that should be used by a given listener in order to enhance the ability of the listener to correctly perceive sound.

While it is common to use a one-to-one mapping scheme between the analysis channels and the stimulus channels, wherein n=m, and the signal analyzed in the first analysis channel is mapped to produce a stimulation current at the first stimulation channel, and so on, it is not necessary to do so. Rather, in some instances, a different mapping scheme may prove beneficial to the patient. For example, assume that n is not equal to m (n, for example, could be at least 20 or as high as 32, while m may be no greater than sixteen, e.g., 8 to 16). The signal resulting from analysis in the first analysis channel may be mapped, using appropriate mapping circuitry 41 or equivalent, to the first stimulation channel via a first map link, resulting in a first stimulation site (or first area of neural excitation). Similarly, the signal resulting from analysis in the second analysis channel of the SP may be mapped to the second stimulation channel via a second map link, resulting in a second stimulation site. Also, the signal resulting from analysis in the second analysis channel may be jointly mapped to the first and second stimulation channels via a joint map link. This joint link results in a stimulation site that is somewhere in between the first and second stimulation sites. The "in between site" is sometimes referred to as a virtual stimulation site. This possibility of using different mapping schemes between n SP analysis channels and m ICS stimulation channels to thereby produce a large number of virtual and other stimulation sites provides a great deal of flexibility with respect to positioning the neural excitation areas in a location that proves most beneficial to the patient.

Still with reference to FIG. 2B, it should be noted that the sound processing circuitry 16 generally includes all of the circuitry from point (C) to point (A). In prior art cochlear implant systems, the entire SP circuitry has been housed in a sound processor that was part of the external (or non-implanted) portion of the system. That is, in such prior art systems, only the ICS 21, and its associated electrode array, were implanted, as indicated by the bracket labeled "Imp1" (for "Implant-1"). This means that in such prior art systems, the signal passing through the serial data stream at point (A) is also the signal that passes through the transcutaneous communication link from the external unit to the implanted unit. Because such signal contains all of the defining control data for the selected speech processing strategy, for all m stimulation channels, it therefore has a fairly high data rate associated therewith. As a result of such high data rate, either the system operation should be slowed down, which is generally not desirable, or the bandwidth of the link should be increased, which is also not desirable because the operating power increases.

In contrast to prior art systems, a modern implant system, such as the CII Bionic Ear system or the HiRes 90K system, manufactured by Advanced Bionics Corporation of Sylmar, Calif., puts at least a portion of the sound processor 16 within the implanted portion of the system. For example, a bionic ear implant may place the Pulse Table 42 and arithmetic logic unit (ALU) 43 inside of the implanted portion, as indicated by the bracket labeled "Imp2" in FIG. 2B. Such partitioning of the sound processor 16 offers the advantage of reducing the data rate that may be passed from the external portion of the system to the implanted portion. That is, the data stream that may be passed to the implanted portion "Imp2" comprises the signal stream at point (B). This signal is essentially the digitized equivalent of the modulation data associated with each of the n analysis channels, and (depending upon the number of analysis channels and the sampling rate associated with each) may be significantly lower than the data rate associated with the signal that passes through point (A). Hence, improved performance without sacrificing power consumption may be obtained with a bionic ear implant.

Future generations of bionic ear implant systems will likely incorporate more and more of the sound processor 16 within the implanted portion of the system. For example, a fully implanted sound processor 16 would incorporate all of the SP in the implanted portion, as indicated by the bracket labeled "Imp3" in FIG. 2B. Such a fully implanted sound processor offers the advantage that the data input into the system, i.e., the data stream that passes through point (C), would need only have rate commensurate with the input acoustic signal.

Figure 3:
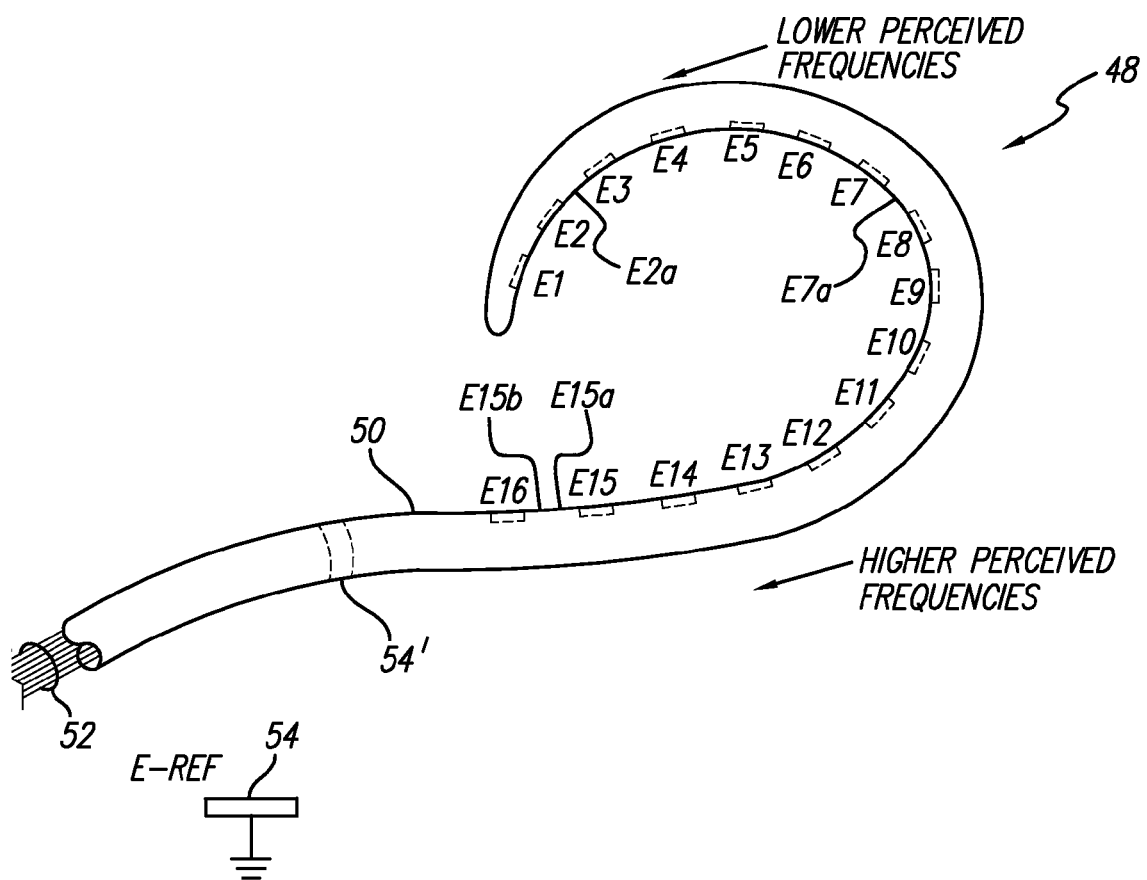
FIG. 3 shows a representative cochlear electrode array, including the spaced-apart electrode contacts thereon, and illustrates the concept of "virtual" electrodes located between physical electrodes, and further illustrates how the array curves in a spiral manner as it is inserted into the cochlea, and wherein when inserted into the cochlea the most distal electrode contacts stimulate neurons that trigger the perception of lower frequency sounds, and wherein the more proximal electrode contacts stimulate neurons that trigger the perception of higher frequency sounds.

Turning next to FIG. 3, an enlarged view of a representative cochlear implant electrode array 48 is illustrated. Such electrode array is adapted to be inserted into a human cochlea so that the auditory nerve may be electrically stimulated. The electrode array 48 has a multiplicity of spaced-apart electrode contacts, E1, E2, E3, . . . Em, carried or embedded within the surface of, an elongate flexible carrier substrate 50. For the electrode array 48 shown in FIG. 3, there are sixteen such electrode contacts, i.e., m=16. Each electrode contact is connected to a respective wire of a bundle 52 of wires that are carried or embedded within the flexible carrier 50. Each wire is connected to appropriate electronic circuitry within the ICS 21 (FIG. 2A) so that a selected current stimulus having a prescribed amplitude, pulse width, and frequency, e.g., a current stimulus having a waveform as shown in FIG. 1, may be applied to body tissue in contact with, or near, the physical location of the electrode contact.

Typically, the current stimulus is applied using monopolar stimulation or bipolar stimulation. In monopolar stimulation, the current stimulus is applied between a selected electrode, e.g., one of the electrode contacts E1, E2, E3, . . . E16, and a reference electrode 54 or 54'. It is common for the reference electrode 54 to be located on the case of the ICS 21, represented in FIG. 3 as the electrode E-REF. In such instance, the reference electrode E-REF is located some distance from the electrode contacts E1, E2, E3, . . . E16. It is also possible for the reference electrode to be a band electrode 54' located proximally on the carrier 50. In bipolar stimulation, the current stimulus is applied between a selected pair of the electrode contacts E1, E2, E3, . . . E16, e.g., between electrode contacts E3 and E4. Multipolar stimulation may also be used where the current stimulus is applied between a selected group of electrode contacts, e.g., between electrode contacts E2, E3 and E5 as anodes, and E4 as a cathode.

It is thus seen that for the electrode array 48 shown in FIG. 3, there are sixteen potential physical stimulus channels through which an electrical stimulus may be applied to the inside of the cochlea. (Other electrode arrays, having fewer or more than sixteen electrode contacts could, of course, also be used.)

It should also be noted, as explained previously, that the ability exists to effectively apply the current stimulus to an "in between site" referred to as a virtual stimulation site. That is, with reference to FIG. 3, the current stimulus can be applied jointly to, e.g., electrode contacts E2 and E3 so as to create a virtual stimulation site at location E2a. The precise location of this virtual stimulation site E2a depends upon how the current stimulus is split between the electrode contacts E2 and E3. If the current stimulus is split more or less equally between the physical electrode contacts E2 and E3 (i.e., if both E2 and E3 function as "anodes" during one phase of the biphasic stimulation pulse, and both function as "cathodes" during the other phase of the biphasic stimulation pulse, and if the amplitude of the current stimulus applied to each electrode contact E3 and E3 is approximately the same), then the virtual stimulation site will lie approximately midway between the location of the physical electrode contacts E2 and E3.

In like manner, still with reference to FIG. 3, a virtual electrode stimulation site E7a may be created approximately midway between physical electrode contacts E7 and E8 by equally sharing a current stimulus between the electrode contacts E7 and E8. Similarly, a plurality of virtual electrode stimulation sites E15a and E15b may be created in between the physical locations of electrode contacts E15 and E16 by sharing the current stimulus between the electrode contacts E15 and E16 in an appropriate ratio.

It is thus seen that through appropriate sharing of stimulus current between selected physical electrode contacts, e.g., by jointly mapping physical stimulus channels, an almost infinite number of virtual stimulus channels, or virtual electrode contacts, may be created. For purposes of the place-pitch ranking procedure described herein, that means that the resolution associated with such procedure, i.e., the ability to accurately measure the spread of perceptual confusion, is greatly enhanced. This measure of the spread of perceptual confusion, in turn, allows the procedure described herein to more optimally determine the number of channels a particular user should employ in order to maximize his or her ability to perceive and understand sounds.

As is well known and documented in the art, the auditory nerve cells which are stimulated through application of an electrical stimulus applied through electrode contacts located inside the cochlea, are arranged tonotopically. That is, these nerve cells are arranged in an orderly tonotopic sequence, from high frequencies at the basal end of the cochlea spiral to progressively lower frequencies towards the apex of the cochlea. Such tonotopically arranged nerve cells may be considered as frequency-sensitive nerves. That is, they comprise a set or family of nerves that are physiologically arranged or located so that higher frequency stimulus signals are perceived differently than lower frequency stimulus signals.

When the electrode array 48 is inserted into the cochlea, a stimulus applied to the more distally-located electrodes should be perceived as a lower frequency tone than would a stimulus applied to the more proximally-located electrodes. Stated differently, a stimulus applied through, e.g., electrode contact E10 should be perceived as a higher frequency tone than would a stimulus applied through electrode contact E8. The present procedure uses this characteristic to systematically identify when there is potential pitch confusion between neighboring stimulus channels, and if so, the extent of such confusion. Once the stimulus channels are identified wherein pitch confusion exists, those channels can be de-selected (not used) by the implant system so as to eliminate or minimize such pitch confusion, thereby assisting the listener (user of the implant device) to better perceive sound.

Hence, the present procedure uses a place-pitch ranking procedure that applies a monopolar stimulus to a first electrode, e.g., electrode Em, followed by applying a stimulus to an adjacent electrode E(m+1). The listener is then asked to rank the pitches perceived. That is, the listener is asked which stimulus, the first or second, elicited the highest perceived pitch, if any. If there is no pitch confusion, the listener should always select the most proximal electrode of the two as the one that elicits the highest pitch. However, if the listener selects the most distal electrode of the two as eliciting the highest pitch, or if the listener cannot discern which of the 1st or second applied stimuli elicits the highest pitch, then there is potential pitch confusion between the two stimulus channels being tested, and additional testing is performed to determine the extent of such confusion.

In accordance with the place-pitch ranking procedure described herein, the implant listener is asked to rank the percepts obtained after a sequential presentation of pulse trains, pulse bursts or noise stimuli are applied to the nerve cells within the cochlea through his or her cochlear implant system. As the stimuli are applied, adjacent channels are stimulated alternately. The choice of electrode contacts through which the stimuli are applied is randomly ordered via a computer-generated sequence. Each electrode pair is interrogated at least 4 times, e.g., two ordinal positions for each of two presentation orders. That is, if the E3-E4 electrode pair is being interrogated, the stimulus is first applied to electrode contact E3 (a first interrogation of the pair), and then to electrode contact E4 (a second interrogation of the pair), and the listener is asked to identify which stimulus (the one from the first interrogation applied to E3, or the one from the second interrogation applied to E4) elicited the highest perceived pitch, or whether both applied stimuli elicited the same perceived pitch. In this manner, the first and second interrogations of the E3-E4 pair provide a response whereby each of the electrodes E3 and E4 are identified as a "H" (highest perceived pitch), a "L" (lowest perceived pitch), or a "S" (same perceived pitch). Then, additional interrogations of the E4-E3 pair are carried out, but with the stimulus being applied first to electrode contact E4 (a third interrogation of the pair), followed by applying the stimulus to electrode contact E3 (a fourth interrogation of the pair). The third and fourth interrogations thus provide a way to further identify each of the electrodes E4 and E3 as a "H", "L" or "S".

Should the patient's judgment of pitch order be correct for all applied interrogations, e.g., for all four combinations, then no further testing involving the tested electrode pair (two electrode contacts) need be undertaken. However, should there be errors in the place-pitch ranking, which errors evidence perceptual place-confusions, then a search is undertaken for the spread of the perceptual confusion by separating the target channel and competing channel by one electrode contact at a time. Because the electrode contacts are spaced apart by a known physical distance, such separation of the target channel and competing channel can be quantified to a known spatial distance. For a cochlear electrode array, the space between the edges of adjacent electrode contacts may be on the order of about 0.9 mm to 1.0 mm, and the electrode contact itself may be about the same distance, e.g., 0.8 to 1.0 mm wide. The search for the spread of confusion continues until no errors are made in all directions.

As mentioned previously, the spread of confusion associated with the place-pitch ranking procedure described herein need not be limited to the physical separation distance of the physical electrode contacts. Rather, virtual electrode contacts may be employed to significantly fine tune what this separation distance may be. In a typical application of the procedure, the physical separation of the stimulus channels is used first as a coarse measure of the spread of confusion. Then, as needed, virtual electrode contacts, or virtual stimulus channels, are used second to provide a more precise or fine measure of the spread of confusion. That is, because virtual electrode contacts may be more finely spaced than the physical electrode contacts, the spread of confusion can be measured using these more finely spaced virtual stimulus channels once a coarse measure of the spread of confusion using the physical stimulus channels has been determined.

Pre-training trials employing channels separated by a large spatial distance (e.g., up to 14 mm) may be employed as needed. During such pre-training trials, a number of "foils" may be introduced during the stimulation procedure wherein the same contact is stimulated twice. This is done in order to separate true perceptual errors from errors in performing the task.

Figure 4A:
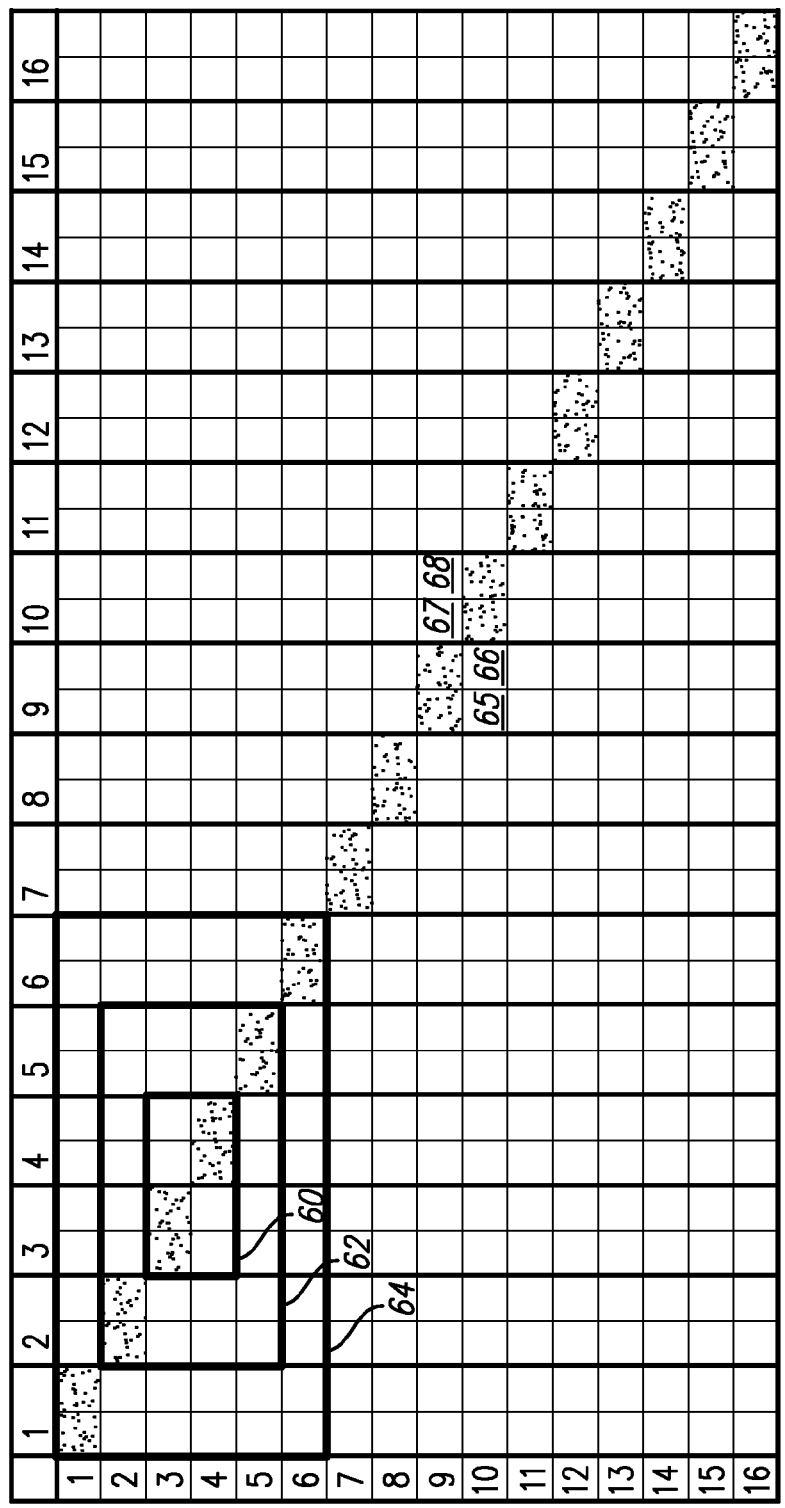
FIG. 4A shows a 16×16 matrix table, or grid, that may be used to gather data in accordance with the adaptive place pitch ranking procedure herein described when an electrode array having 16 electrode contacts is used.

Responses obtained during the stimulation procedure may be recorded on a grid after each stimulus pair has been presented. A representative grid of the type that may be employed is shown in FIG. 4A. Each cell in the grid is subdivided into two subparts, where each subpart corresponds to the 1st or 2nd pulse of an applied stimulus sequence. Thus, for example, for the electrode pair E9-E10, a stimulus is applied first to E9 and a second stimulus is applied to E10, in that order, and the listener is asked to identity which of the applied stimuli (the first pulse applied to E9 or the second pulse applied to E10) has the highest perceived pitch. If the first pulse is perceived as the highest pitch, then an "H" may be placed in the first subpart 65 of the cell of the matrix corresponding to the E9 column where it intersects with the E10 row. Such response also means that a "L" may be placed in the second subpart 66 of the same cell, i.e., the second pulse was perceived as the lowest pitch.

Continuing with the example for the electrode pair E9-E10, a stimulus will next be applied first to E10 and a second stimulus will be applied to E9, in that order, and the listener is again asked to identify which of the applied stimuli (the first pulse applied to E10 or the second pulse applied to E9) has the highest perceived pitch. If the second pulse is perceived as the highest pitch, then an "H" may be placed in the second subpart 68 of the cell corresponding to the Ex10 column where it intersects with the E9 row. Such a response also means that a "L" may be placed in the first subpart 67 of the same cell because the first pulse was perceived as the lowest pitch.

Thus, it is seen that each electrode pair that is interrogated is represented by a first area 60 of the grid. (The area 60 shown in FIG. 4A corresponds, by way of example, to the E3-E4 electrode pair.) The area 60 comprises the intersection of the E3 and E4 electrodes in the grid. The cell corresponding to the E3 column and E4 row, with its two subparts, is used to record the response for the applied stimulation corresponding to an order of stimulation where the E3 electrode is stimulated first and the E4 electrode is stimulated second. The cell corresponding to the E4 column and E3 row, with its two subparts, is used to record the response for the applied stimulation corresponding to an order of stimulation where the E4 electrode is stimulated first and the E3 electrode is stimulated second. Thus, with reference to the example of the cell of the grid corresponding to the E3 column-E4 row, the first subpart of the cell, reading left to right, provides a location where the response corresponding to the first pulse may be recorded, and the second subpart of the cell provides a location where the response corresponding to the second pulse may be recorded. Similarly, with reference to the example of the cell of the grid corresponding to the E4 column-E3 row, the first subpart of the cell, reading left to right, provides a location where the response corresponding to the first pulse may be recorded, and the second subpart of the cell provides a location where the response corresponding to the second pulse may be recorded.

As potential perceptual confusion is identified, the area expands so as to increase the physical distance between the target electrode contact and a competing electrode contact by an integral number of contacts. For example, a second area 62 is shown in FIG. 4A that represents the E2-E5 electrode pair separated by two electrode contacts. A third area 64 is shown that represents the E1-E6 electrode pair separated by four electrode contacts.

Turning next to FIG. 4B, a gird, or grid table, of the type shown in FIG. 4A is illustrated, but with exemplary response data placed therein. As seen in the example data of FIG. 4B, for electrode pairs E4-E5, E5-E6, E6-E7, E7-E8, . . . E15-E16, there is no perceptual confusion. Thus, once this determination is made, no further testing of these electrode pairs is needed. This greatly reduces the amount of response data that might otherwise be required in order to test all possible electrode pairs.

In contrast, the exemplary response data of FIG. 4B shows that the errors in pitch perception surrounding electrode E1 (stimulus channel 1) extend all the way to stimulus channel 4 (electrode E4) regardless of which contact is stimulated first or second. Thus, assuming a typical electrode spacing of a cochlear electrode, the pitch confusion extends over some 3.5 to 4.0 mm of distance. Similar pitch confusions are seen for channels 2, 3 and 4 (E2, E3 and E4). Given this pitch confusion, the sound processor of the implant system may be programmed not to use stimulus channels 1 through 4. In that way, the listener (user of the device) will not be forced to struggle through discerning sounds for which the perceived pitch is not correct.

Alternatively, as desired, virtual channels may be employed to refine the spread of confusion measurement determined as outlined above. That is, once it has been determined that pitch confusion exists all the way from physical electrode contact E1 to physical electrode contact E4, a distance of some 3.5 to 4.0 mm, virtual electrode contacts (virtual stimulus channels) may be used to better (more precisely) measure this distance. For example, through the use of such virtual stimulus channels, it may be determined that the spread of confusion actually exists only between a point about ¾ of the way between electrode contact E1 and E2, a location referred to, e.g., as E1.75, and a point about ¼ of the way between electrode contact E3 and E4, a location referred to as E3.25. Thus, the spread of confusion is really only about 2.0 to 2.5 mm, or 1.5 mm less than the coarse measure obtained using the physical stimulus channels. Hence, rather than not using (or "deselecting") stimulus channels E1 through E4, it may be possible, through use of, e.g., virtual stimulus channels E1.5 and E3.5 (virtual channels that are selected to be close to, but not exactly the same as the measured E1.75 and E3.25 boundary points), as well as physical stimulus channels E1 and E4, to deselect only physical stimulus channels E2 and E3, thereby providing enhanced ability to the user to better perceive sounds and pitches.

Those of skill in the art will recognize that the exemplary grids of FIG. 4A and FIG. 4B represent only one manner in which response data may be gathered and analyzed. Numerous other techniques may be used to gather, assemble or analyze response data, including computerized methods or manual methods, any of which could be used with the present procedure.

For example, in cases where a cochlear implant recipient does not have a concept of pitch (e.g., children), or where a cochlear implant recipient's concept of pitch is emerging (e.g., pre-lingually deafened adults), the procedure allows for alternate methods of recording responses to establish an estimate of which channels might produce similar place-pitch percepts and thus negatively impact performance. Such responses may include, but are not limited, to a "same-different" response.

Figure 5:
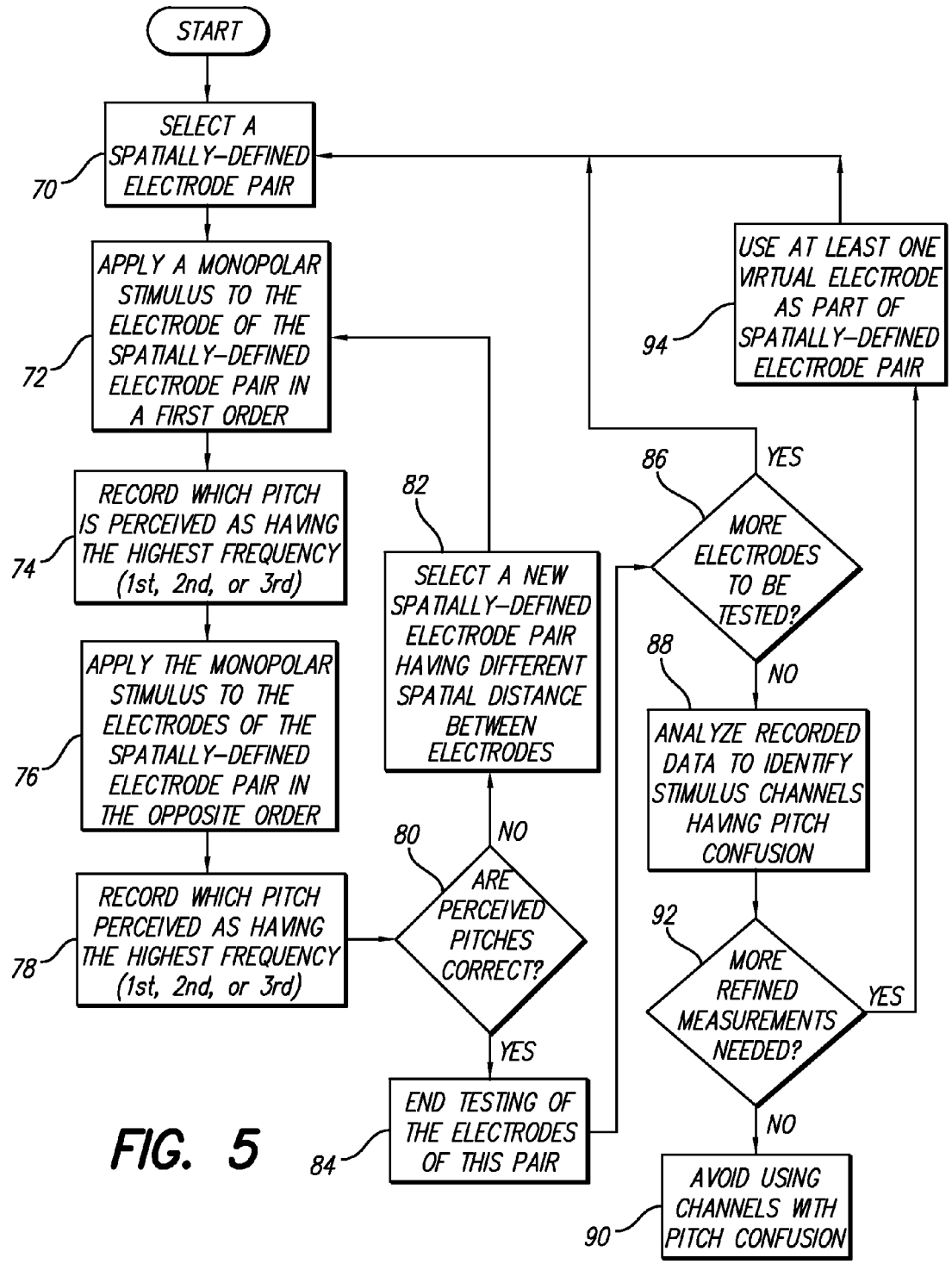
FIG. 5 is a flow chart that depicts one manner in which the adaptive place-pitch ranking procedure may be performed.

Next, with reference to FIG. 5, a high level flow chart is illustrated that shows one manner in which the present procedure may be carried out. As seen in FIG. 5, a spatially-defined electrode pair is first defined (block 70). Typically, at least initially, such electrode pair will be adjacent physical electrodes, e.g., having a spatial separation of only about one millimeter. Although, as previously indicated, in some instances, e.g., when conducting pre-training trials, an electrode pair may be selected having a large spatial separation (e.g., up to 14 mm). In other instances, a virtual electrode pair (where a "virtual electrode pair" means at least one electrode of the pair is a virtual electrode) may be selected having a smaller spatial separation, or at least a spatial separation that is more finely defined than the 1 mm increments associated with the physical electrodes. Thus, by using a virtual electrode pair, the spatial separation could be, e.g., 0.5 mm, 1.75 mm, or 2.75 mm, rather than just 1 mm, 2 mm or 3 mm.

Once the spatially-defined electrode pair has been identified, a monopolar stimulus is applied to the electrodes of the spatially-defined electrode pair in a first order (block 72). For example, if the defined electrode pair comprises electrode contacts E1 and E2, then such electrode pair is stimulated so that E1 is stimulated with a first stimulus pulse, and E2 is stimulated with a second stimulus pulse, so that the stimulation order is E1, E2. The response data from such stimulation is then recorded (block 74). Such response data identifies, e.g., which of the stimulation pulses is perceived as having the highest frequency ("H"), and which is perceived as having the lowest frequency ("L"). In some instances, the perceived frequency elicited from the stimulation pulses may be the same ("S"). Hence, the response data takes the form of "H", "L", or "S". Alternatively, as indicated above, the response data for some patients, e.g., where the patient does not have a concept of pitch, may be a "same-different" response, where the data may take the form of "S" (same) or "D" (different), or any other appropriate symbol that indicates same or different.

Next, the monopolar stimulus is applied to the same spatially-defined electrode pair, but with the stimulus being applied in a different order (block 76). Thus, if the defined electrode pair comprises electrode contacts E1 and E2, and if previously the stimulation order was E1 followed by E2, then this time the stimulus pulse is applied first to E2 and then second to E1. Response data from such stimulation is again recorded (block 78) so that, e.g., the stimulus pulse perceived as having the highest ("H"), lowest ("L"), or the same ("S") frequency is recorded, or so that the stimulus pulse perceived as being the same ("S") or different ("D") is recorded.

After the response data has been gathered for a given spatially-defined electrode pair, a determination is made as to whether the perceived pitches are correct (block 80). Correct pitch perception results when stimulation of the most distally-located electrodes are perceived as the lowest pitches, and when stimulation of the most proximally-located electrodes are perceived as the highest pitches.

If there is pitch confusion (NO branch of block 80), then a new spatially-defined electrode pair is selected having a different spatial distance between the electrodes (block 82), and the above-described process (blocks 72-80) is repeated. Usually, at least when doing coarse measurements not involving a virtual electrode pair, the spatial distance is increased. In some instances, however, particularly when fine measurements are being made involving a virtual electrode pair, the spatial distance may be decreased.

If there is no pitch confusion (YES branch of block 80), then the testing for the electrodes in that spatially-defined electrode pair is concluded (block 84), and if there are other electrode pairs to be tested (YES branch from block 86), such electrode pairs are tested using the same procedure (blocks 70-84).

If all electrode pairs have been tested (NO branch from block 86), then the recorded response data is analyzed to identify those stimulus channels where pitch confusion is present (block 88). Based on the results of this analysis, a decision may be made as to whether a more refined measurement is needed or desired (block 92). If so (YES branch from block 92), then a virtual electrode pair is defined (block 94) involving at least one virtual electrode, and the process is repeated (blocks 70-88.) If not (NO branch from block 92), then the channels where pitch confusion exists may then be de-selected (not used) by the implant system (block 90) during its normal operation, thereby enhancing the user's ability to better perceive the sound presented to his or her cochlear implant.

One of the illustrative features of the adaptive place-pitch ranking procedure described herein is that it allows the procedure to be carried out in a time frame that is clinically feasible. To illustrate, a representative cochlear implant has an electrode array that contains sixteen spaced-apart electrode contacts. Any of these sixteen contacts, in combination with a return or reference electrode contact (which could be located, e.g., on the case of the ICS, or could be any of the remaining fifteen electrode contacts) may thus provide a stimulation electrode pair that could be used in a high resolution mode of stimulation. If place-pitch ranking were to be performed by testing all sixteen electrode contacts against all other electrode contacts (a 16×16 matrix), the procedure would take more time than would be clinically feasible. Sample tests performed on 4 subjects have indicated that testing all sixteen stimulation channels against all other channels would consume approximately 2 hours of time. In contrast, by using the adaptive place-pitch ranking procedure described herein, the time is reduced to 15-20 minutes (depending upon the extent of perceptual place-confusions).

Hence, it is seen that the time to perform the adaptive place-pitch ranking procedure is reduced to a clinically-feasible time.

Figure 6:
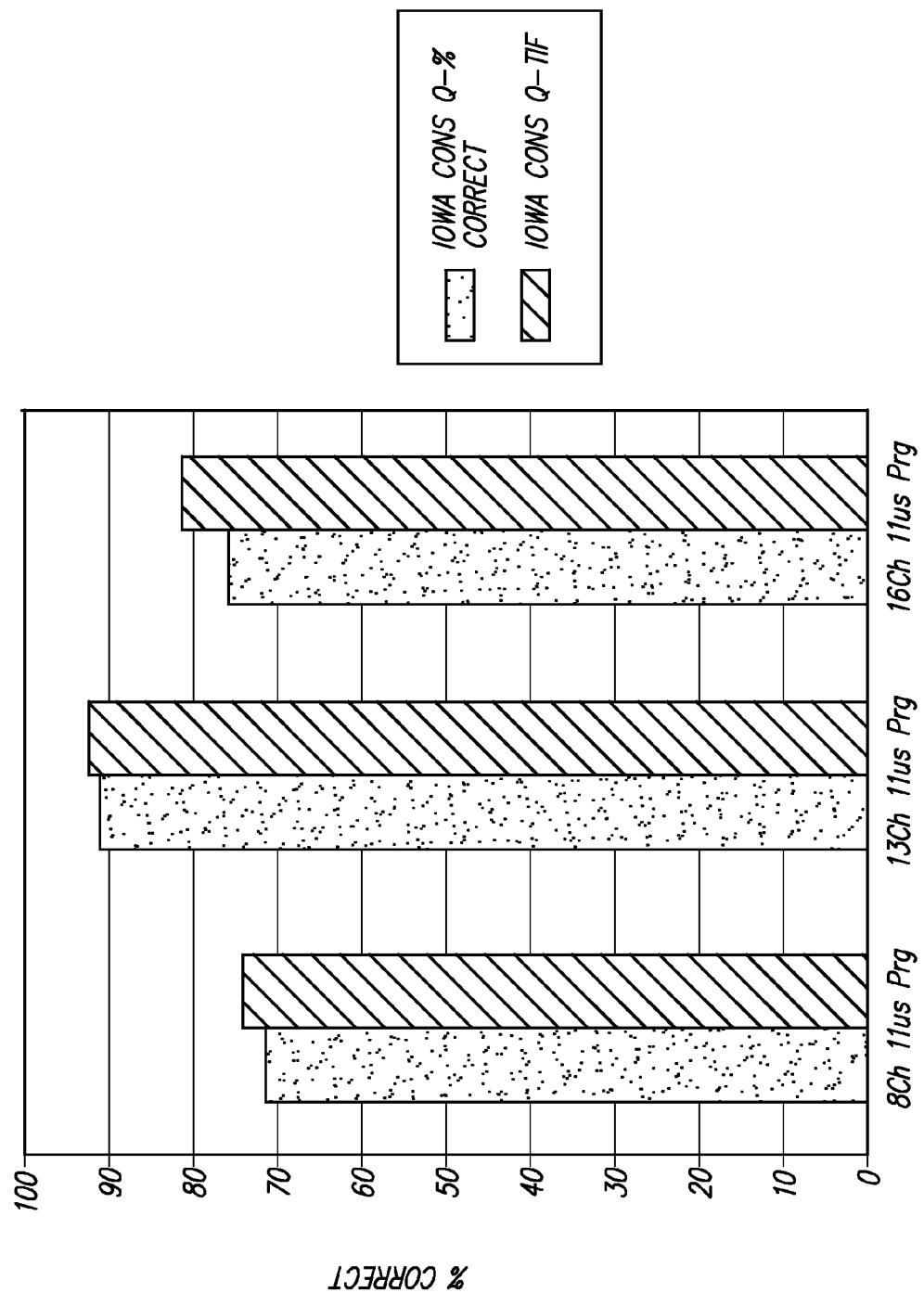
FIG. 6 is a table that presents data illustrating the improvement in patient performance obtained using the place pitch ranking procedure herein described.

FIG. 6 provides an example of how the performance of the user may be improved through use of the present procedure. FIG. 6 is a chart that illustrates the performance of a subject user (patient). The subject was first fitted with his cochlear implant system in such a way that the speech spectrum was divided among either 8 channels or 16 channels. The subject was blind to the number of channels in his processor at the time of speech perception testing. Speech perception testing involved the use of well-characterized speech stimuli and test procedures. The Iowa Consonant Test was administered and scored for percent correct, and Total Information Transfer (TIF) expressed as a percent. While performance was not significantly better with 16 channels than with 8 channels, the subject reported that he felt that his performance was better with a program that unbeknownst to him had 8 stimulation channels vs. 16 channels. However, after the present procedure was used to optimize the number of channels that would be best for the subject to use (i.e., to identify those channels where there was pitch confusion, and to de-select such channels), the subject was re-tested. After using the procedure, it was determined that 13 channels would be the optimum number of channels to use for this particular subject. Again, the subject's performance with this programming change due to use of the proposed procedure was validated by formal speech perception testing.

As indicated in FIG. 6, when the subject was stimulated using only 8 channels at a pulsewidth of 11 µs/ph and was tested using well characterized speech stimuli (consonant tokens in a /vCv/ context), the subject scored 71% and 73% correct for actual percent correct and total information transfer, respectively. When the subject was stimulated on all 16 channels with the same 11 µs/ph pulsewidth and assessed with the same speech materials, the subject scored 76% and 81% correct for actual percent correct and total information transfer, respectively. These sets of scores were not significantly different from each other. However, when the subject was stimulated on 13 channels (i.e., when the channels confused for pitch were identified through use of the place-pitch ranking procedure and were removed), using 11 µs/ph pulses and the same speech tests, the subject scored 91% and 92% for actual percent correct and total information transfer, respectively.

Thus, it is seen from the data presented in FIG. 6 that through use of the place-pitch ranking procedure described herein to identify and remove those stimulus channels where pitch confusion occurred, the subject was able to significantly improve his performance.

Appendix A provides an overview of one embodiment of a Fitting System that may be used with the procedure described herein. The adaptive place-pitch ranking procedure described herein may readily be carried out by incorporating an appropriate software module incorporated within such fitting system. That is, through use of the fitting system described in Appendix A, it is seen that a selected signal may be generated and applied to a first selected electrode and then to a second selected electrode. Moreover, as previously indicated, the first and/or second selected electrodes may be either physical or virtual electrodes, as needed or desired. This capability allows a clinician to manually carry out the place-pitch ranking procedure. However, through appropriate software control incorporated within the fitting system, many of the procedures associated with carrying out the steps may be automated, or semi-automated, in order to facilitate use of the procedure.

While the procedure herein disclosed has been described by means of specific embodiments and applications thereof, numerous modifications and variations could be made thereto by those skilled in the art without departing from the scope of the invention set forth in the claims.

What is claimed is:

1. A method for measuring the spread of perception confusion between stimulus channels of a neural stimulation system comprising:

coarsely determining the spread of perception confusion using physical stimulus channels; and finely determining the spread of perception confusion using at least one virtual stimulus channel;

wherein coarsely determining the spread of perception confusion using physical stimulus channels comprises (a) sequentially applying monopolar stimulation pulses in a first order to a selected spatially-defined physical electrode pair representing adjacent stimulus channels;

(b) sequentially applying monopolar stimulation pulses in a second order to the selected spatially-defined physical electrode pair;

(c) ranking perceived sounds resulting from the stimulation pulses applied in the first order and the second order;

(d) determining whether the perceived sounds are correct, and if so, ceasing further testing involving the selected spatially-defined physical electrode pair, and (e) if the perceived sounds are not correct, identifying a state of perceived confusion for the spatially-defined electrode pair, defining a new spatially-defined physical electrode pair representing stimulus channels that are one stimulus channel farther apart than the previously defined physical electrode pair, and (f) repeating steps (a)-(e) as many times as necessary to determine the spread of confusion as measured in terms of a physical separation between stimulus channels.

2. The method of claim 1 wherein finely determining the spread of perception confusion using at least one virtual stimulus channel comprises (a) sequentially applying monopolar stimulation pulses in a first order to a selected spatially-defined virtual electrode pair, said virtual electrode pair including at least one virtual electrode contact, said virtual electrode pair having a separation distance between electrode contacts, at least one of which electrode contacts is a virtual electrode contact, that is measured in terms of units that are fraction of the physical separation between stimulus channels;

(b) sequentially applying monopolar stimulation pulses in a second order to the selected spatially-defined virtual electrode pair;

(c) ranking perceived sounds resulting from the stimulation pulses applied in the first order and the second order;

(d) determining whether the perceived sounds are correct, and if so, ceasing further testing involving the selected spatially-defined virtual electrode pair, and (e) if the perceived sounds are not correct, identifying a state of perceived confusion for the spatially-defined virtual electrode pair, defining a new spatially-defined virtual electrode pair and a new separation distance between electrode contacts of the virtual electrode pair that is a different distance than the separation distance of the previously defined virtual electrode pair, and (f) repeating steps (a)-(e) as many times as necessary to determine the spread of confusion between stimulus channels as measured in terms of a virtual stimulus channel separation.

3. The method of claim 2 wherein finely determining the spread of perception confusion using at least one virtual stimulus channel includes recording responses obtained during application of the monopolar stimulation pulses on a grid table.

4. The method of claim 3 further including dividing each cell in the grid table into at least two subparts and recording responses obtained during application of the stimulation pulses in each subpart.

5. The method of claim 1 wherein coarsely determining the spread of perception confusion using physical stimulus channels includes recording responses obtained during application of the monopolar stimulation pulses on a grid table.

6. The method of claim 5 further including dividing each cell in the grid table into at least two subparts and recording responses obtained during application of the stimulation pulses in each subpart.

* * * * *